United States Patent [19]

Hewawasam et al.

[11] Patent Number: 5,158,958
[45] Date of Patent: Oct. 27, 1992

[54] IMIDAZO[4,5-B]QUINOLINYL OXY ALKYL SULFONYL PIPERIDINE DERIVATIVES

[75] Inventors: Piyasena Hewawasam, Middletown; Nicholas A. Meanwell, East Hampton, both of Conn.

[73] Assignee: Bristol-Myers Squibb Company, New York, N.Y.

[21] Appl. No.: 863,278

[22] Filed: Apr. 3, 1992

[51] Int. Cl.$^5$ .................. C07D 471/04; A61K 37/47
[52] U.S. Cl. ........................ 514/293; 546/82
[58] Field of Search ............... 546/82; 514/293

[56] References Cited

U.S. PATENT DOCUMENTS

| | | |
|---|---|---|
| 3,932,407 | 1/1976 | Beverung, Jr. et al. |
| 4,256,748 | 3/1981 | Chodnekar et al. |
| 4,490,371 | 12/1984 | Jones et al. |
| 4,668,686 | 5/1987 | Meanwell et al. |
| 4,701,459 | 10/1987 | Meanwell et al. |
| 4,775,674 | 10/1988 | Meanwell et al. |
| 4,943,573 | 7/1990 | Meanwell. |

FOREIGN PATENT DOCUMENTS 153152 of 1985 European Pat. Off.

OTHER PUBLICATIONS

Barrera, et al., *J. Org. Chem.*, 27: 641 (1962).
S. Seiler, et al., "Imidazoquinoline Derivatives: Potent Inhibitors of Platelet cAMP Phosphodiesterase which elevate cAMP levels and Activate Protein Kinase in Platelets", *Thromb. Res.*, 62: 31-42 (1991).
Kozak, et al., *Bull. Intern. Acad. Polanaise*, 1930A: 432-438 (Che. Abs. 25, 5400).
J. S. Fleming, et al., New Drugs Annual: Cardiovascular Drugs, Raven Press, 277-294, NY (1983).
J. S. Fleming, J. O. Buchanan, S. M. Seiler, and N. A. Meanwell, "Antithrombotic Acticity of BMY 43351, a New Imidazoquinoline wiht Enhanced Aqueous Solubility", *Thromb. Res.*, 63: 145-155 (1991).

*Primary Examiner*—C. Warren Ivy
*Assistant Examiner*—Barbara Twardzik
*Attorney, Agent, or Firm*—Michelle A. Kaye

[57] ABSTRACT

A novel series of 1,3-dihydro-2H-imidazo [4,5-b]quinolin-2-ones having enhanced water solubility bioavailability and metabolic stability is disclosed in the Formula I

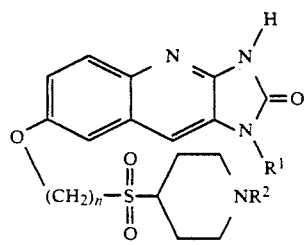

wherein
$R^1$ is H, or $C_1$-$C_4$ lower alkyl;
$R^2$ is H, or $(CH_2)_m R^3$;
$R^3$ is tetrahydro-2H-pyranyl, $C_1$-$C_8$ alkyl, $C_4$-$C_8$ cycloalkyl, or substituted or unsubstituted phenyl in which the substituents are halogen, alkoxy, or trifluoromethyl;
m is an integer of 1-3; and n is an integer of 1-5; or pharmaceutically acceptable salt thereof.

The compounds are useful as inhibitors of ADP-induced blood platelet aggregation in human platelet-rich plasma.

20 Claims, No Drawings

IMIDAZO[4,5-B]QUINOLINYL OXY ALKYL SULFONYL PIPERIDINE DERIVATIVES

BACKGROUND OF THE INVENTION

1. Field of the Invention

This invention relates to a new class of selective and potent inhibitors of platelet cyclic AMP phosphodiesterase. In particular, the invention relates to a series of new sulfonylpiperidine derivatives of imidazo[4,5-b]quinolin-2-one which are useful as inhibitors of adenosine diphosphate-induced aggregation of human blood plateletes in platelet-rich-plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, intracranial tumors, thromboembolism, and hyperlipemia (A. Poplawski, et al, *J. Atherosclerosis Research*, 8: 721 (1968)).

The imidazo[4,5-b]quinolin-2-one derivatives have been identified as potent inhibitors of human blood platelet cAMP phosphodiesterase (PDE) and in vitro aggregation induced by ADP and collagen (Seiler *et al*, *Thromb. Res.*, 62, 31–42 (1991).

The heterocycle "2,3-dihydro-2-oxo-1H-imidazo[4,5-b]quinoline" of the formula (1), alternately referred to as 1,3-dihydro-2H-imidazo [4,5-b]quinolin-2-one, was described by Kozak, *et al*, *Bull. Intern. Acad. Polanaise*, 1930A, 432-438 (Chem. Abs. 25, 5400).

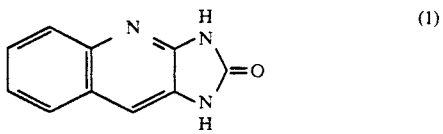

Derivatives of formula (1) having cyclic AMP phosphodiesterase inhibitory activity have been prepared and studied for their platelet inhibition and cardiotonic properties. Thus, for example:

Meanwell, N. A., U.S. Pat. No. 4,943,573 describes a series of 2,3-dihydro-2-oxo-1H-imidazo[4,5-b]quinolin-2-ones comprising derivative of the formula (2)

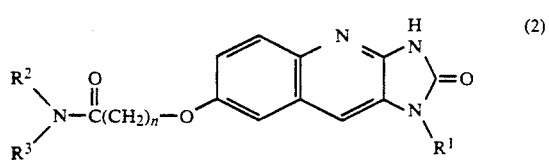

wherein n is 3 to 5; $R^1$ is hydrogen or alkyl of 1 to 4 carbon atoms; $R^2$ is hydrogen; $R^3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl; $R^2$ and $R^3$ together with the nitrogen atom to which they are attached form 4-$R^4$-piperazin-1-yl wherein $R^4$ is alkyl of 1 to 7 carbon atoms, alkoxyethyl of 3 to 7 carbon atoms, pyridinyl, pyrimidinyl, tetrahydropyranylmethyl, thienylmethyl, cycloalkyl-$(CH_2)_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms.

Among the compounds disclosed is the compound of the formula (3), identified as 1-(cyclohexylmethyl) -4-(2,3-dihydro-2-oxo-1H-imidazo[4,5-b]quinolin-7-yloxy)-oxybutyl]piperazine.

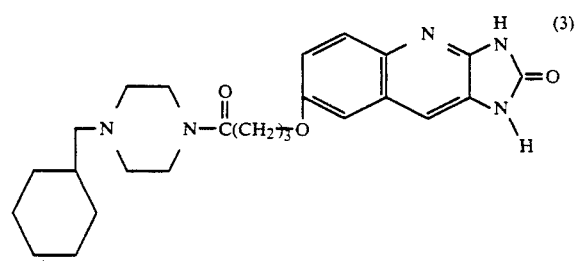

Meanwell, et al. U.S. Pat. No. 4,775,674 describe a series of 2,3-dihydro-2-oxo-1H-imidazo[4,5-b]quinolinyl ether derivatives of the formula (4)

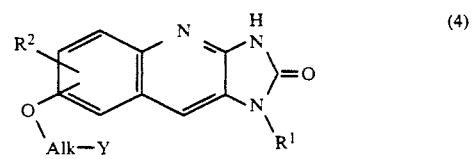

wherein $R^1$ is hydrogen, lower alkyl, benzyl; $R^2$ is hydrogen, halogen, lower alkyl, lower alkoxy; Alk is alkylene; Y is hydroxy and alkanoic or aralkanoic esters thereof, oxo ketone, dialkylamino carboxylic acid and esters, carboxamides, alkoxy, ethanolamines and cyclic carbamates thereof, tetrazoyl, and optionally substituted phenylsulfonyl.

Among the compounds disclosed is the compound of formula (5), identified in the art as 7-[4-(phenylsulfonyl)butoxy]-1,3-dihydro-2H-imidazo[4,5-b]quinolin-2-one.

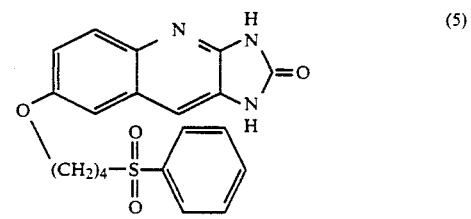

Meanwell, et al, U.S. Pat. No. 4,701,459 describe another series of 2,3-dihydro-2-oxo-1M-imidazo-[4,5-b]quinoline compounds comprising amine derivatives of formula (6)

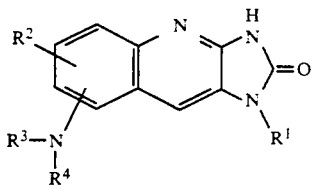

(6)

wherein R¹ is hydrogen, lower alkyl; R² is hydrogen, lower alkyl, lower alkoxy, halogen; R³ is hydrogen, lower alkyl; R⁴ is hydrogen, lower alkyl, alkanoyl, phenylalkanoyl wherein phenyl is optionally substituted with halogen, lower alkyl, lower alkoxy, R³ and R⁴ are joined together to form morpholinyl, piperidinyl or pyrrolidinyl optionally substituted with —CO₂R⁵ or

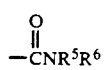

R⁵ is hydrogen or lower alkyl, and R⁶ is hydrogen, lower alkyl, cycloalkyl; 4-R⁷-piperazinyl wherein R⁷ is —CO₂R⁸ wherein R⁸ is lower alkyl, phenyl optionally substituted with up to 2 halogen, lower alkyl or lower alkoxy phenylalkanoyl of 7 to 10 carbon wherein phenyl is unsubstituted or independently substituted with up to 2 halogen, lower alkyl, lower alkoxy.

Meanwell, et al, U.S. Pat. No. 4,668,686 describe still another series of 1,3-dihydro-2M-imidazo-[4,5-b]quninolin-2-ones comprising derivatives of formula (7)

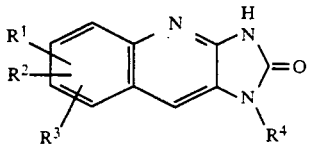

(7)

wherein R¹ is halogen, lower alkyl, lower alkoxy, trifluoromethyl; R² is hydrogen, halogen, lower alkyl, lower alkoxy; R³ is hydrogen, halogen, lower alkyl, lower alkoxy; and R⁴ is hydrogen or lower alkyl.

Another class of heterocyclic compounds having phosphodiesterase inhibiting and anti-platelet aggregation activity comprise the tetrahydroimidazo[2,1-b]quinazolin-2-ones of formula

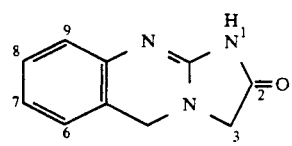

(8)

For example:

Beverung, Jr., et al, U.S. Pat. No. 3,932,407 disclose a series of compounds useful as blood platelet antiaggregative and/or antihypertensive and/or bronchodilator agents of tetrahydroimidazo[2,1b]-quinazolin-2-one class. Anagrelide (9), a particularly preferred member of the Beverung, Jr., et al. series, has been studied extensively, e.g., J. S. Fleming, et al, New Drugs Annual: Cardiovascular Drugs, Raven Press, 277–294, NY (1983).

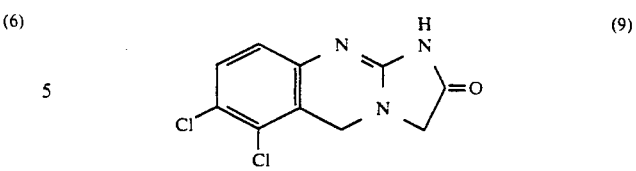

(9)

Chodnekar, et al, U.S. Pat. No. 4,256,748 describe a series of tetrahydroimidazo[2,1-b]quinazolin-2-ones of the formula (10) as inhibitors of the aggregation of blood platelets and cardiotonic activity.

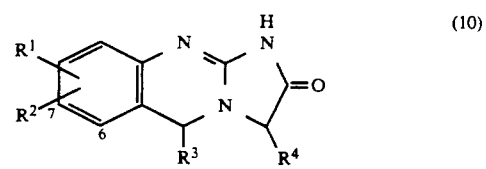

(10)

Representative of the Chodneker compounds are RO 15-2041 (R⁴=CH₃, R³=H, R²=6-CH₃, R¹=7-Br) and RO 13-6438 (R⁴=CH₃, R³=H, R²=6-CH₃, R¹=H).

Jones, et al, U.S. Pat. No. 4,490,371 describe another series of tetrahydroimidazo[2,1-b]quinazolin-2-one derivatives as cyclic AMP phosphodiesterase inhibitors useful as thrombogenic agents. Among the compounds disclosed is the formula (11) amide, identified in the art as lixazinone.

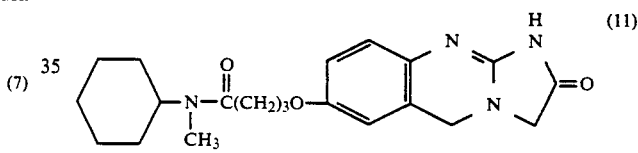

(11)

Jones, et al, European Patent Application 153152 further describe tetrahydroimidazo[2,1-b]quinazoline-ones of formula (11) as cyclic AMP phosphodiesterase inhibitors useful as antithrombogenic agents.

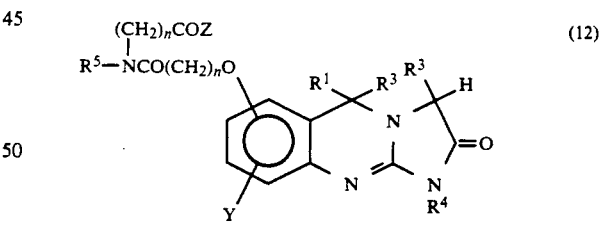

(12)

Compounds of the aforementioned patents generally display limited solubility in water, acidic or alkali media and common organic solvents.

SUMMARY OF THE INVENTON

The present invention provides novel sulfonylpiperidine derivatives of imidazo [4,5-b]quinolin-2-one which have enhanced potency and aqueous activity.

In particular, the invention relates to a series of 7-oxy-propylsulfonyl-1,3-dihydro-2Mimidazo[4,5b]quinolin-2-ones wherein the phenyl ring substituent of the formula (5) compounds were replaced with a piperidine moiety. The basic nitrogen atom of the piperidine ring provides a second site for salt formation resulting in enhanced potency and water solubility compared to the formula (5) compounds.

Formula I illustrates the compounds of the invention and the ring numbering system used herein.

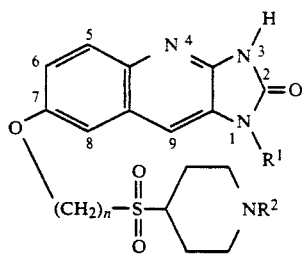

Formula I

In the foregoing Formula I, n, $R^1$, and $R^2$ are as described below.

The compounds of Formula I are useful as inhibitors of adenosine diphosphate-induced aggregation of human blood platelets in platelet rich plasma.

The compounds of Formula I have antithrombogenic and phosphodiesterase inhibition properties and are useful in prevention or treatment of conditions involving platelet aggregation and thrombosis.

The compounds of Formula I are also considered to have antimetastatic potential in view of their platelet inhibition properties.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

DETAILED DESCRIPTION OF THE INVENTION

The compounds of the instant invention comprise those of Formula I,

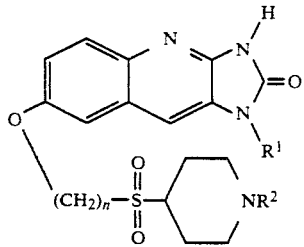

Formula I wherein
$R^1$ is H, or $C_1$–$C_4$ lower alkyl;
$R^2$ is H, or $(CH_2)_m R^3$;
$R^3$ is tetrahydro-2H-pyranyl, $C_1$–$C_8$ akyl, $C_4$–$C_8$ cycloalkyl, or substituted or unsubstituted phenyl in which the substituents are halogen, alkoxy or trifluoromethyl;
m is an integer of 1–3, and
n is an integer of 1–5; or pharmaceutically acceptable salt thereof. It is understood that as used herein limitation of Formula I are defined as follows:

The term "halogen" comprehends fluorine, iodine, bromine and chlorine, and most preferably fluorine and chlorine.

The term "$C_1$–$C_4$ lower alkyl" refers to a branched or unbranched saturated hydrocarbon chain containing from 1 to 4 carbon atoms, specifically, methyl, ethyl, n-propyl, isopropyl, butyl, isobutyl.

The term "$C_1$–$C_8$ alkyl" refers to a branched or unbranched saturated hydrocarbon chain containing from 1 to 8 carbon atoms, for example, methyl, ethyl, n-propyl, isopropyl, butyl, isobutyl, 3-pentyl and 4-heptyl.

The term "$C_4$–$C_8$ cycloalkyl" comprehends a saturated aliphatic ring containing the designated number of carbon atoms. Such radicals are, for example, cyclobutyl, cyclopentyl, cyclohexyl, cycloheptyl, and cyclooctyl.

According to the present invention, the compounds characterized by Formula I and the pharmaceutically acceptable acid addition salts thereof, were prepared as outlined in Schemes I and II.

Commercially available 1-methyl-4-piperidone (1) was converted to corresponding gem-dithiol (H. Barrera and R. E. Lyle, *J. Org. Chem.*, 27, 641 (1962)) 2 by reaction with hydrogen sulfide in isopropanol. Reduction of the dithiol 2 with sodium borohydride ($NaBH_4$) in isopropanol gave 1-methyl-4-mercaptopiperidine (3). (H. Barrera and R. E. Lyle, *J. Org. Chem.*, 27, 641(1962)). Reaction of the thiol 3 with ethyl chloroformate followed by neutralization with aqueous ammonium hydroxide ($NH_4OH$) afforded 1-methyl-4-(ethoxycarbonyl)-mercaptopiperidine (4). Demethylation of 4 with ethyl chloroformate gave S,N-bis-ethoxycarbonyl-piperidine-thiol (5). Selective deprotection of the thiocarbamate moiety of 5 with sodium ethoxide (NaOEt) followed by in-situ reaction of the resultant thiolate with 1-chloro-3-iodopropane gave chloropropyl substituted piperidinethiol derivative 6a. Oxidation of the sulfide 6a with peracetic acid in dichloromethane ($CH_2Cl_2$) gave the corresponding sulfone 7a.

Scheme II

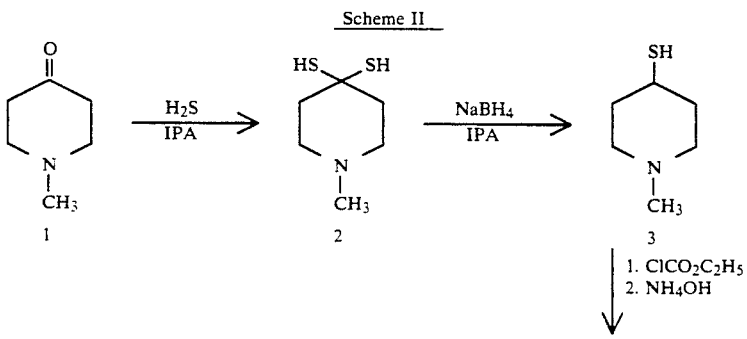

Scheme II

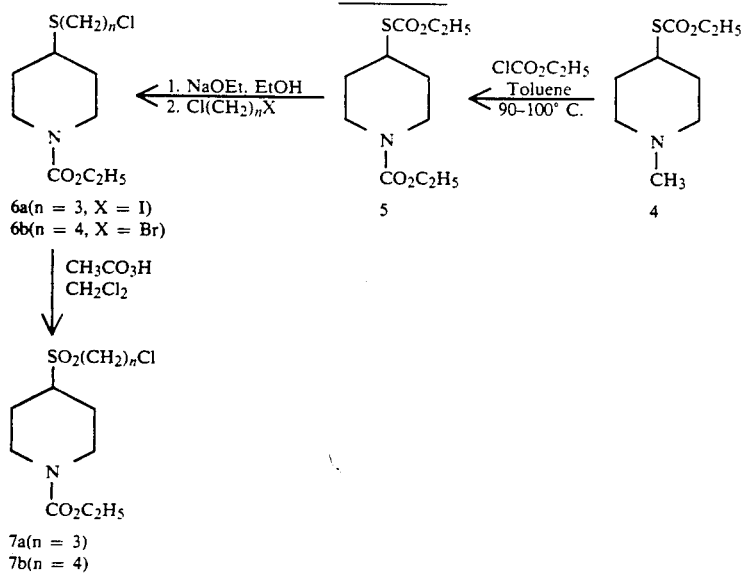

6a(n = 3, X = I)
6b(n = 4, X = Br)

7a(n = 3)
7b(n = 4)

Subsequent steps of the synthesis were carried out as outlined in Scheme II. O-Alkylation of 5-hydroxy-2-nitrobenzaldehyde with the chloropropylsulfone derivative 7a provided the nitrobenzaldehyde derivative 8a. Condensation of anion of the phosphonate with the aldehyde 8a afforded the isomeric mixture of hydantoin derivatives 10a,a'. Exhaustive catalytic hydrogenation over 10% palladium on activated carbon (Pd-C) followed by cyclization and concomitant oxidation using $I_2$ in dimethylformamide (DMF) provided the target imidazoquinolin 13a. Basic hydrolysis of the carbamate moiety of 13a furnished the N-H congener 14a which was alkylated with variety of alkylating agents in the presence of triethylamine as the acid scavenger. Finally the target imidazoquinolines were converted to their hydrochloride salts by reacting with anhydrous hydrogen chloride in methanol.

Scheme II

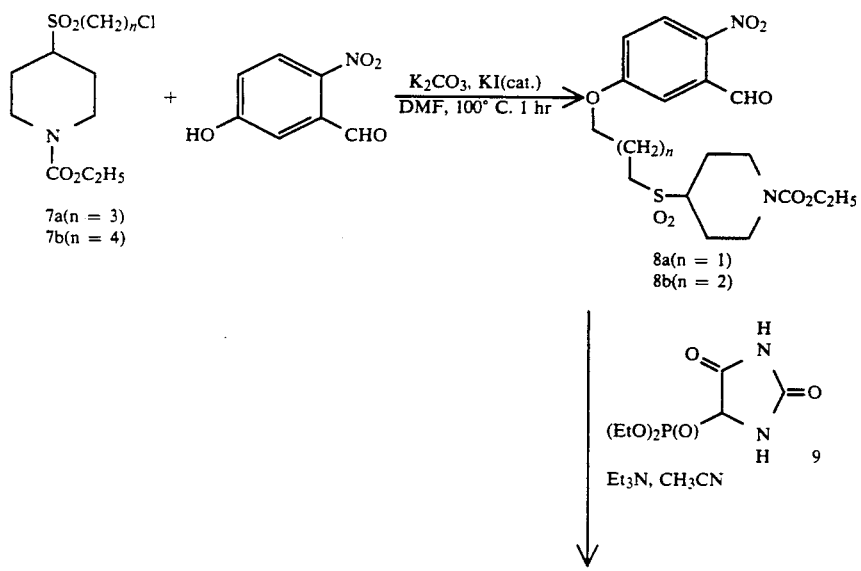

7a(n = 3)
7b(n = 4)

8a(n = 1)
8b(n = 2)

-continued
Scheme II

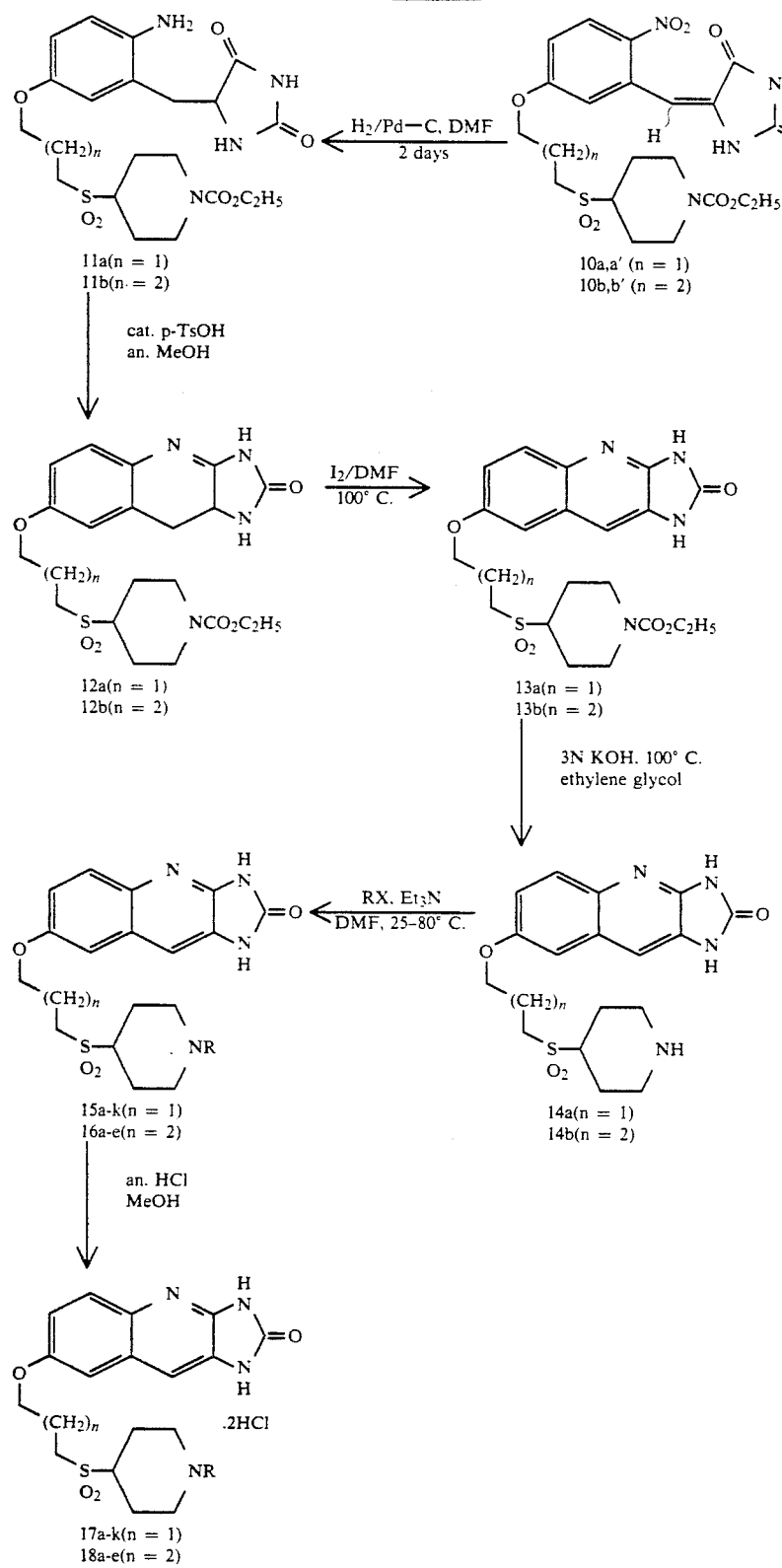

In Vitro Inhibition of Human Platelet Agregation

The aggregometer method of Born, G.V.R., *J. Physiol.*, (London), 162, 67–68, (1962) as modified by Mustard, J. F., et al., *J. Lab. Clin. Med.*, 64, 548–599, (1964) was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube containing 3.8% sodium citrate to prevent clotting (1 part citrate to 9 parts blood).

Platelet rich plasma (PRP) was separated by centrifugation for 10 minutes at 1000 rpm (140xg) from citrated (3.8%) human blood. All glassware used for preparation of PRP is silicon treated. ADP in final concentration of 0.5 µg/mL or 0.05 mL of a collagen suspension prepared according to the method described by Evans, G., et al., J. Exp. Med., 128, 877-894, (1968) was used to induce aggregation. The various compounds tested were dissolved in dimethylsulfoxide (DMSO) so that 5 µl added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 µg/ml vs. ADP and 245 µg/ml vs collagen. Results for 50% inhibition of ADP-induced aggregation are given hereinafter.

The target compounds were evaluated as inhibitors of ADP-induced aggregation of human blood platelets in platelet-rich-plasma (PRP) in vitro. The test compounds were incubated at about 37° C. in PRP for about 3 minutes prior to the addition of sufficient ADP to provide a final ADP concentration of 5.86 mM.

TABLE I

Inhibition of ADP-induced Human Platelet Aggregation by Test Compounds

| Cmpd # | $IC_{50}$ vs ADP in human PRP, µg/mL | Aqueous Solubility mg/mL |
| --- | --- | --- |
| 13a | 0.3 | 0* |
| 13b | 0.2 | 0* |
| 17a | >32 | >10 |
| 18a | 7.4 | >10 |
| 17b | 0.014 | >10 |
| 18b | 0.024 | ~5 |
| 17c | 0.012 | >10 |
| 18c | 0.04 | ~2 |
| 17d | 0.018 | <10 |
| 18d | 0.018 | ~2 |
| 17e | 0.022 | <10 |
| 18e | 0.012 | ~5 |
| 17f | 0.014 | >10 |
| 17g | 0.028 | <5 |
| 17h | 0.074 | <5 |
| 17i | 0.024 | <5 |
| 17j | 0.14 | ~1 |
| 17k | 0.02 | >10 |

*Aqueous Solubility of Free Base

The Formula I compounds or pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient. Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the does of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

1-Methyl-4-mercaptopiperidine (3)

Hydrogen sulfide was introduced in a vigorous current with stirring into a cold (0° C.) solution of freshly distilled 1-methylpiperidine (80 g, 0.71 mol) in isopropanol (200 mL). Temperature of the reaction was maintained at about 0°-5° C. Excess hydrogen sulfide ($H_2S$) was allowed to pass through a sodium hypochlorite solution (chlorox ®) followed by sodium hydroxide solution in series. After about 1 hour precipitated white solid was filtered off to yield 118.5 g of gem-dithiol. Filtrate was treated with $H_2S$ gas for about 2 hours to give 26.0 g of additional dithiol. Filtrate from second crop was treated with $H_2S$ for about 2-3 hours at about −5° to 0° C. and then gas flow was stopped and stirred overnight. Filtration of the resultant suspension gave 21.5 g of additional dithiol to provide combined yield of 66 g (51.5%). Crude gem-dithiol was dried over phosphorus pentoxide ($P_2O_5$) in a dessicator in the dark. Crude product was reduced with ($NaBH_4$) without further purification.

To a cold (0°-5° C.) stirred suspension of $NaBH_4$ (11.0 g, 0.29 mol) in isopropanol (100 mL), gem-dithiol (44 g, 0.243 mol) was added in small portions under nitrogen. After the addition is complete, resultant suspension stirred at about 0°-5° C. for about 0.5 hour, and then allowed to warm to room temperature and stirred overnight. Reaction mixture was heated to about 80° C. over about 30 minutes and then maintained for about 2 hours. Allowed to cool to about 40°-45° C. and then isopropanol was rotary-evaporated under reduced pressure. Resultant white pasty residue was mixed with ether (100 mL) and cold water (20 mL) was added to dissolve the suspension. Clear bi-phase mixture was stirred for about 5-10 minutes and then layers were separated. Aqueous layer was reextracted with ether (2×100 mL). Combined ether extracts were washed with brine and then dried sodium sulfate ($Na_2SO_4$). Ether was rotary evaporated (at 100 torr and 35°-40° C. bath temperature) to give light yellow oil (33 g) which was distilled in vacuo to afford 25.8 g (81%) of pure 1-methyl -4-mecarptopiperidine: bp 30°-35° C./0.04-0.05 torr; IR (Film, $cm^{-1}$) 3000-2800, 2678, 1446, 1376; $^1$H NMR (300 MHz, $CDCl_3$) δ1.42 (1H, d, J=7.0 Hz), 1.53 (2H, m), 1.89 (4H, m), 2.13 (3H, s), b 2.66 (3H, m); $^{13}$C NMR (75 MHz, $CDCl_3$) δ35.79, 37.17, 46.37, 55.55; MS m/e 132 (MH+), 98;

Anal. calcd. for $C_6H_{13}NS$:
C, 54.91; H, 9.98; N, 10.67.
Found: C, 54.38; H, 9.99; N, 10.29.

EXAMPLE 2

1-Methyl-4-(ethoxycarbonylmercapto)piperidine (4)

To a stirred solution of 1-methyl-4-mercaptopiperidine (25 g, 0.19 mol) in anhydrous , acetone (200 mL), ethyl chloroformate (23.2 g, 0.123 mol) was added dropwise over about 25-30 minutes. During the addition pot temperature was maintained between about 15°-20° C. Resultant suspension was stirred at room temperature under nitrogen for about 2 hours. Hydrochloride salt was filtered off and washed consecutively with acetone and ether. Concentration of combined filtrate and washings followed by addition of anhydrous ether gave additional salt. Combined solid was dried in vacuo to give 44.2 g (97%) of hydrochloride salt of the desired product. The salt was suspended in ether (150 mL) and treated with water with stirring. Resultant biphase mixture was neutralized with saturated ($NH_4OH$). Layers were separated and the aqueous layer was re-extracted with ether (2×150 mL). Combined ether extracts were washed with brine and then dried ($Na_2SO_4$). Evaporation of ether gave a colorless oil which was distilled in vacuo to afford 33.7 g (87.1%) of pure 2: bp 60°-62° C./0.01 torr; IR (Film, $cm^{-1}$) 3000-2800, 1704, 1144, 1378; $^1$H NMR (300 MHz, $CDCl_3$) δ 1.21 (3H, t, J=7.2 Hz), 1.63 (2H, m), 1.94 (2H, m), 2.06 (2H, m), 2.17 (3H, s), 2.64 (2H, m), 3.23 (1H, m), 4.17 (2 H, q, J=7.2 Hz); $^{13}$C NMR (75 MHz, $CDCl_3$) δ 14.40, 32.51, 41.60, 46.43, 55.21, 63.35, 170.46; MS m/e 204 (MH+).

Anal calcd. for $C_{19}H_{17}NO_2S$:
C, 53.17; H, 8.43; N, 6.89.
Found: C, 53.47; H, 8.66; N, 6.86.

EXAMPLE 3

1-Ethoxycarbonyl-4-(ethoxycarbonylmercapto) piperidine (5)

Ethyl chloroformate (35.2 g, 0.32 mol) was added dropwise over about 30 minutes to a stirred and heated (90° C.) solution of 1-methyl-4-(ethoxycarbonyl mercapto)piperidine (33.0 g, 0.16 mol) in dry toluene (35 mL). The resultant mixture was then heated to about 100°-110° C. for about 2 hours. After this period additional ethyl chloroformate (12 mL) was added dropwide and then continued to heat at about 100°-110° C. for additional 3 hours. Reaction mixture was allowed to cool to room temperature and stand overnight. The resultant suspension was filtered off and the filtrate was washed with toluene. Combined filtrate and washings were rotary evaporated to remove the toluene and then residue was distilled in vacuo to give 37.0 g (87.3%) of pure 5: bp 116°-118° C./0.01 torr; IR (Film, $cm^{-1}$) 1702, 1252, 1144, 1388; $^1$H NMR (300 MHz, $CDCl_3$) δ 1.18 (3H, t, J=7.1Hz), 1.23 (3H, t, J=7.1H), 1.52 (2H, m), 1.95 (2H, m), 3.02 (2H, m), 3.40 (1H, m), 3.90 (2H, m), 4.03 (2H, q, J=7.1Hz), 4.19 (2H, q, J=7.1Hz); $^{13}$C NMR (75 MHz, $CDCl_3$) δ 14.44, 14.84, 32.13, 41.98, 43.49, 61.52, 63.63, 155.50, 170.14; MS m/e 262 (MH+).

Anal. calcd. for $C_{11}H_{19}NO_4S$:
C, 50.56; H, 7.33; N, 5.36.
Found: C, 50.70; H, 7.29; N, 5.36.

EXAMPLE 4

1-Ethoxycarbonyl-4-[(3-chloropropyl)mercaptol piperidiene (6a)

A solution of 21% wt. NaOEt in absolute ethanol (40.9 g, 0.126 mol) was added dropwise over about 15 minutes to a stirred cold (0°-5° C.) solution of 1-ethoxycarbonyl-4-(ethoxycarbonylmercapto)piperidine (5) (30.0 g, 0.115 mol) in absolute ethanol (50 mL). Resultant mixture was allowed to warm to ambient temperature and stirred for about 2-3 hours. Reaction mixture was cooled in an ice bath and then 1-chloro-3-iodopropane (25.8g, 0.126 mol) was added over about 15 minutes. The mixture was allowed to warm to room temperature and then stirred overnight (22 hours). To the reaction mixture, ether (200 mL) and 50% saturated brine (100 mL) were added and then stirred for about 5-10 minutes. Layers were separated and the aqueous layer was re-extracted with ether (2×200 mL). Combined ether extracts were washed with water, brine and then dried (Na$_2$SO$_4$). Filtration followed by evaporation of the ether gave 31.7 g of crude material. Crude product was flash chromatographed (silicia gel; 40% EtOAc in hexanes) to afford 30.3 g (99%) of pure 6a: IR (Film, cm$^{-1}$) 1700, 1470, 1432, 1250, 1114; $^1$H NMR (300 MHz, CDCl$_3$) δ 1.20 (3H, t, J=7.1Hz), 1.46 (2H, m), 1.89 (2H, m), 1.99 (2H, m), 2.65 (2H, t, J=7.0H), 2.76 (1H, m), 2.92 (2H, m), 3.60 (2H, t, J=6.2Hz), 3.96 (2H,m), 4.07 (2H, q, J=7.1Hz); $^{13}$C (75 MHz, CDCl$_3$) δ 14.87, 27.18, 32.57, 32.64, 41.35, 43.46, 43.68, 61.49, 155.58; MS m/e 266.

Anal. Calcd. for C$_{11}$H$_{20}$ClNO$_2$S:
C, 49.71; H, 7.58; N, 5.27.
Found: C, 49.70; H, 7.71; N, 5.19.

EXAMPLE 5

1-Ethoxycarbonyl-4-(3-chloropropanesulfonyl)piperidine (7a)

Peracetic acid in acetic acid (32% wt., 57 g, 50.5 mL, 0.24 mol) was added dropwise over about 30 minutes to a cold (−20° C.) stirred solution of 1-ethoxy-carbonyl-4-[(3-chloropropyl)mercapto]piperidine (29.0 g, 0.11 mol) in CH$_2$Cl$_2$ (500 mL). After the addition is complete the mixture was allowed to warm to room temperature and then stirred for about 5 hours. Reaction mixture was cooled in an ice bath and then quenched with 10% sodium sulfite (Na$_2$SO$_3$) solution (200 mL). Layers were separated and the aqueous layer was reextracted with CH$_2$Cl$_2$ (250 mL). Combined CH$_2$Cl$_2$ extracts were washed with saturated sodium bicarbonate (NaHCO$_3$) solution (300 mL), water, brine and then dried magnesium sulfate (MgSO$_4$). Filtration followed by rotary evaporation of CH$_2$Cl$_2$ gave a viscous oil which was kept in vacuo overnight to afford 32.6 g (100%) of white crystalline sulfone 7a: mp 49°-51° C., IR (KBr, Cm$^{-1}$) 1696, 1300, 1254, 1126; $^1$H NMR (300 MHz, CDCl$_3$) δ 1.19 (3H, t, J=7.Hz), 1.69 (2H, m), 2.07 (2H, m), 2.27 (2H, m), 2.75 (2H, m), 2.97 (1H, m), 3.05 (2H, t, J=7.4 Hz), 3.64 (2H, t, J=6.0 Hz), 4.07 (2H, q, J=7.1 Hz), 4.28 (2H, m); $^{13}$C NMR (75 MHz, CDCl$_3$) δ 14.80, 24.56, 24.67, 42.73, 43.27, 46.85, 59.62, 61.82, 155.28; MS m/e 298 (MH+).

Anal. calcd. for C$_{11}$H$_{20}$ClNO$_4$S:
C, 44.37; H, 6.77; N, 4.70.
Found: C, 44.19; H, 6.68; N, 4.77.

EXAMPLE 6

Ethyl 4-3-(3-formyl-4-nitrophenoxy)propyl sulfonyl -1-piperidinecarboxylate (8a)

A stirred suspension of 5-hydroxy-2nitrobenzaldehyde (18 g, 0.017 mol), 1-ethoxycarbonyl-4-(3-chloropropanesulfonyl) piperidine (32 g, 0.017 mol), pulverized anhydrous potassium carbonate (K$_2$CO$_3$) (17.8 g, 0.12° mol) and KI (3.6 g, 0.02 mol) in anhydrous DMF (120 mL) was heated at about 100°-110° C. under nitrogen for about 1.25 hours. Reaction mixture was allowed to cool to about 50°-60° C. and most of the DMF was rotary evaporated under reduced pressure (50° C. bath temperature). Resultant viscous residue was suspended in CH$_2$Cl$_2$ (200 mL) and then water was added with stirring. Layers were separated and the aqueous layer was re-extracted with CH$_2$Cl$_2$ (2×200 mL). Combined CH$_2$C$_2$ extracts were washed consecutively with 10% sodium carbonate (Na$_2$CO$_3$) (2×200 mL), water, brine and then dried (MgSO$_4$). Filtration followed by rotary evaporation of CH$_2$Cl$_2$ gave a viscous oil which was kept in vacuo overnight. The resultant semi-solid was triturated with warm ether and with good agitation to produce a finely divided solid which was filtered, washed with ether and then dried in Vacuo to give 41.8 g (91.3%) of pure 8a: mp 101°-103° C.; IR (KBr, cm$^{-1}$) 1696, 1508, 1344, 1310, 1264, 1256, 1134, 848; $^1$H NMR (300 MHz, CDCl$_3$) δ 1.23 (3H, t, J=7.11Hz), 1.75 (2H, m), 2.11 (2H, m), 2.41 (2H, m), 2.79 (2H, m), 3.05 (1H, m), 3.13 (2H, t, J=7.2 H), 4.11 (2H, q, J=7.1 Hz), 4.26 (2H, t, J=5.9 Hz), 4.33 (2H, m), 7.13 (1H, dd, J=9.0 and 2.8 Hz), 7.28 (1H, d, J=2.8 Hz), 8.13 (1H, d, J=9.0Hz), 10.43 (1H, s); $^{13}$C NMR (75 MHz, CDCl$_3$) δ 14.83, 21.34, 24.80, 42.78, 46.05, 59.94, 61.92, 67.13, 114.21, 118.87, 127.58, 134.51, 142.76, 155.32, 162.90, 188.51; MS m/e 429 (MH+).

Anal. calcd. for C$_{18}$H$_{24}$N$_2$O$_8$S:
C, 50.46; H, 5.65; N, 6.64.
Found C, 50.52; H, 5.61; N, 6.64.

EXAMPLE 7

Ethyl 4-[[3-[(2-,3-dihydro-2-oxo -1H-imidazo [4,5-b]quinolin-7-yl)oxy] propylsulfonyl]-1-piperidinecarboxylate 13a

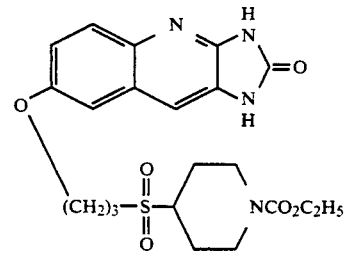

A solution of the aldehyde 8a (37.0 g, 0.086 mol) in acetonitrile (250 mL) was added dropwise over about 30 minutes, to a stirred partial solution of the phosphonate 9 (24.5 g, 0.103 mol) and isoamylamine (Et$_3$N) in acetonitrile (125 mL). The resultant deep-red solution was stirred at room temperature for about 5 hours. Excess Et$_3$N and acetonitrile were rotary evaporated under reduced pressure at about 50° C. bath temperature. Resultant viscous brown-red oil was treated with about 0.05 N HCl with mechanically stirring. Initially formed gummy lumps gradually breaks up into a finely divided solid upon good agitation. Solid was filtered off and washed with water and then air dried overnight to afford about 45.7 g of crude product which was hydrogenated without further purification.

Hydrogenation was carried out in three equal batches. A suspension resulted from addition of 10% Pd-C (0.75 g) to a solution of the nitro-olefins 10a,a' (15 g) in DMF (250 mL) was hydrogenated in a Parr apparatus under 60-70 psi for about 19 hours. Then additional fresh Pd-C (0.75 g) was added and continued for additional 32 hours. Since TLC and NMR analysis showed incomplete reduction, additional fresh Pd-C (0.75 g) was added and continued for additional 20 hours. The suspension was filtered through a pad of celite and the celite pad was washed thoroughly with DMF. Combined filtrate and washings were rotary evaporated under vacuum at about 50° C. bath temperature, to afford a viscous semi-solid which was kept in vacuo overnight to afford about 56 g of crude product.

Crude keto-aniline derivative 11a (56 g) and p-toluenesulfonic acid (2.0 g) were suspended in anhydrous methanol (1 L) and then heated to reflux for about 20 hours. Resultant gray suspension was allowed to cool, filtered, washed with methanol and then air dried to give about 36.6 g (89.5% overall for two steps) of desired dihydroimidazoquinoline derivative 12a.

To a stirred hot (100°-105° C.) suspension of 12a in DMF (900 mL), iodine was added in small portions. Upon addition of $I_2$, suspension gradually dissolves. Resultant brown solution was maintained at about 100°-105° C. for about 1.25 hours. Reaction mixture was allowed to cool to about 50°-60° C. and then DMF was rotary evaporated (2-3 torr/50° C. bath temperature). Resultant viscous residue was cooled and neutralized with saturated $NaHCO_3$ solution and then treated with about 10% $Na_2S_2O_3$ solution (300 mL) with vigorous stirring until iodine color disappears. Resultant brown-gray suspension was filtered off and washed with water and then air dried overnight. Crude product was triturated with boiling methanol to give about 35.2 g (98.7%) of title compound 13a: mp 318°-321° C.; IR (KBr, cm$^{-1}$) 1720, 1696, 1388, 1366, 1260, 1220, 1130, 824: $^1$H NMR (300 MHz, DMSO-d$_6$) δ 1.15 (3H, t, J=7.0Hz), 1.46 (2H, m), 2.01 (2H, m), 2.18 (2H, m), 2.81 (2H, m), 3.27 (2H, t, J=7.6Hz), 3.42 (2H, m), 4.01 (2H, q, J=7.0 Hz), 4.07 (1H, m), 4.16 (2H, t, J=6 Hz), 7.15 (1H, dd, J=9.1 and 2.7Hz), 7.31 (1H, d, J=2.7 Hz), 7.50 (1H, s), 7.67 (1H, d, J=9.1Hz), 10.96 (1H, s), 11.37 (1H, s); $^{13}$C NMR (75 MHz, DMSO-d$_6$) δ 14.58, 21.18, 23.98, 42.11, 45.84, 57.06, 60.88, 65.81, 107.42, 109.45, 117.99, 126.10, 126.44, 128.19, 138.17, 145.47, 154.41, 154.48, 155.42; MS m/e 463 (MH+).

Anal. calcd. for $C_{21}H_{26}N_4O_6S$:
C, 54.53; H, 5.66; N, 12.11.
Found: C, 54.42; H, 5.61; N, 11.89.

EXAMPLE 8

4-[[3-[[(2-,3-Dihydro-2-oxo

-1H-imidazo[4,5-b]guinolin 7-yl)oxy]propylsulfonyl]piperidine dihydrochloride 17a

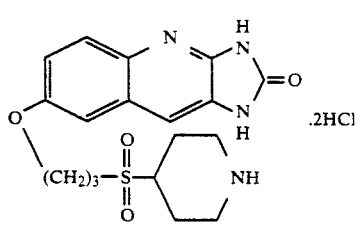

A stirred solution of the carbamate 13a (34 g 0.07 mol) in ethylene glycol (200 mL) and 3N KOH (100 mL) was heated at about 100°-110° C. under nitrogen for about 46 horus. Reaction mixture was allowed to cool to room temperature and then acidified with 3N HCl to pH3. Finally, pH of the resultant suspension was adjusted to 7-8 with saturated $NaHCO_3$ solution. Precipitated product was filtered and washed with water and then air dried for about 2 days. Crude product was triturated with boiling methanol to give about 28.2 g (98.3%) o pure 14a. A small sample of the free base 14a was converted to the dihydrochloride salt 17a by reacting with anhydrous HCl/MeOH.

17a: mp 340°-345° C.; IR (KBr, cm$^{-1}$) 3600-2300, 1744, 1298, 1236, 1130, 824: $^1$H NHR (300 MHz, DMSO-d$_6$) δ 1.89 (2H, m), 2.17 (4H, m), 2.89 (2H, m), 3.33 (4H, m), 3.53 (1H, m), 4.18 (2H, t, J=6 Hz), 7.20 (1H, dd, J=9.1 and 2.7Hz), 7.38 (1H, d, J=2.7Hz), 7.61 (1H, s), 7.76 (1H, d, J=9.1Hz), 8.0 (1H, brd s), 9.13 (1H, brd s), 9.49 (1H, brd s) 11.23 (1H, s); $^{13}$C NMR (75 MHz, DMSO-d$_6$)δ 21.15, 21.29, 41.64, 46.20, 54.41, 65.86, 107.74, 110.72, 118.50, 125.57, 126.24, 126.68, 135.96, 144.87, 154.71, 155.12; MS m/e 391 (MH+).

Anal. calcd. for $C_{18}H_{22}N_4O_4S.2HC 1.1.2H_2O$:
C, 44.58; H, 5.49; N, 11.55.
found: C, 44.59; H, 5.13; N, 11.03.

EXAMPLE 9

4-[[3-[2,3-Dihydro-2-oxy

-1H-imidazo[4,5-b]quinolin-7-yloxy]

propyl]sulfonyl]-1-(phenylmethyl)piperidine dihydrochloride 17b

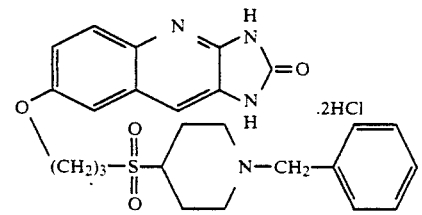

mp 282°-285° C.; IR (KBr, cm$^{-1}$) 3600-2200, 1724, 1294, 1240, 1130, 825, 746, 700: $^1$H NMR (300 MHz, DMSO-d$_6$) δ 2.19 (6H, m), 2.93 (2H, m), 3.31 (2H, t, J=6.0OHz), 3.45 (3H, m), 4.16 (2H, t, J=6.0Hz), 4.27 (2H, m) 7.16 (1H, dd, J=9.1 and 2.7Hz), 7.34 (1H, d, J=2.7Hz), 7.44 (3H, m), 7.54 (1H, s), 7.60 (2H, m), 7.70 (1H, d, J=9.1Hz), 11.09 (1H, s), 11.23 (1H, brd s), 11.52 (1H, brd s); $^{13}$C NMR (75 HMHz, DMSO-d$_6$) δ 22.92, 23.35, 48.02, 51.27, 56.24, 60.46, 67.52 109.26, 111.63, 119.87, 126.99, 128.07, 129.34, 120.47, 131.15, 131.22, 133.30, 139.08, 146.97, 156.20, 157.01; MS m/e 481.

Anal. calcd. for $C_{25}H_{28}N_4O_4S.2HCl.0.7H_2O$:
C, 52.98; H, 5.60; N, 9.90.
Found: C, 52.99; H, 5.59; N, 10.05.

EXAMPLE 10

4-[[3-[2,3-Dihydro-2-oxo 1H-imidazo[4,5-b]quinolin-7 piperidine dihydrochloride 17c

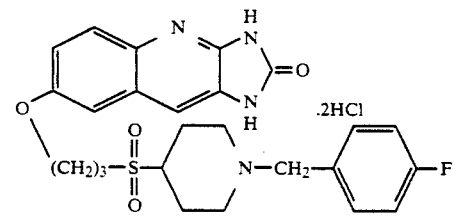

mp 308°-311° C.; IR (KBr, cm$^{-1}$) 3600-2300, 1750, 1230, 1132, 820: $^1$H NMR (300 MHz, DMSO-d$_6$) δ 2.12 (6H, m), 2.92 (2H, m), 3.31 (2H, t, J=7.6Hz), 3.44 (3H, m), 4.17 (2H, t, J=6.0Hz), 4.27 (2H, m), H, dd, J=9.1 and 2.7Hz), 7.28 (2H, d, J=8.9 and 8.6Hz), 7.38 (1H, d, J=2.7Hz), 7.61 (1H, s), 7.68 (2H, dd, J=8.6 and 3.1 Hz), 7.75 (1H, d, J=9.1 Hz), 1.24 (1H, s), 11.40 (1H, brd s), 11.66 (1H, brd s); $^{13}$C NMR 75 MHz DMSO-d$_6$) δ 22.92, 23.34, 48.01, 51.11, 56.25, 67.56, 109.41, 112.3, 117.21, 117.50, 120.20, 127.25, 127.41, 127.94, 128.40, 135.65, 137.72, 146.58, 156.39, 156.83; MS m/e 499.

Anal. calcd. for C$_{25}$H$_{27}$FN$_4$O$_4$S.2HCl.1.3H$_2$O:
C, 50.40; H, 5.36; N, 9.40.
Found: C, 50.39; H, 5.17; N, 9.37.

EXAMPLE 11

4-[[3-[2,3-Dihydro-2-oxo
-1H-imidazo[4,5-b]quinolin-7
-yl-oxy]propyl]sulfonyl]-(cyclohexylmethyl)
piperidine dihydrochloride 17d

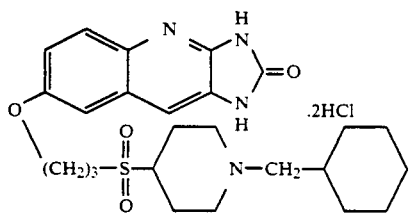

mp 310°-313° C.; IR (KBr, cm$^{-1}$) 3600-2300, 1726, 1296, 1240, 1128, 826; $^1$H NMR (300 MHz, DMSO-d$_6$) δ 0.88 (2H, m), 1.10 (3H, m), 1.59 (3H, m), 1.74 (3H, m), 2.07 (6H, m), 2.83 (2H, t, J=5.7Hz), 2.91(2H, m), 3.30 (2H, m), 3.47 (1H, m), 3.57 (2H, m), 4.15 (2H, J=6.0Hz), 5.08 (2H, brd s), 7.15 (1H, dd, J=9.1 and 2.7 Hz), 7.33 (1H, d, J=2.7Hz), 7.53 (1H, s), 7.68 (1H, d, J=9.1Hz), 9.78 (1H, brd s), 11.07 (1H, s); $^{13}$C NMR (75 MHz, DMSO-d$_6$) δ 21.41, 21.62, 24.98, 25.48, 30.58, 32.09, 46.30, 50.84, 54.51, 62.19, 65.85, 107.63, 110.05, 118.24, 125.34, 126.37, 127.52, 137.20, 145.24, 154.56, 155.29; MS m/e 487.

Anal. calcd. for C$_{25}$H$_{34}$N$_4$O$_4$S.2HCl.1.9H$_2$O:
C, 50.57; H, 6.76; N, 9.44.
Found: C, 50.57; H, 6.44; N, 9.51.

EXAMPLE 12

4-[[3-[2,3-Dihydro-2-oxo
-1H-imidazo[4,5-b]quinolin-7
yl-oxy]propyl]sulfonyl]1-(2-ethylbut
-1yl)piperidine dihydrochloride 17e

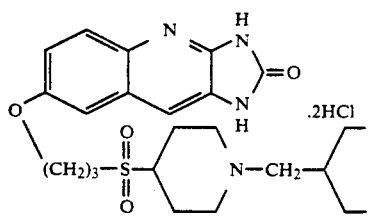

mp 261°-264° C.; IR (KBr, cm$^{-1}$) 3600-2300, 1720, 1296, 1364, 1242, 1128, 825; $^1$H NMR (300 MHZ, DMSO-d$_6$) δ 0.79 (6H, t, J=7.3Hz), 1.32 (4H, m), 1.67 (1H, m), 2.14 (6H, m), 2.87 (2H, t, J=6.0Hz), 2.93 (2H, m), 3.31 (2H, m), 3.44 (1H, m), 3.59 (2H, m), 4.15 (2H, t, 7.13 (1H, dd, J=9.1 and 2.7Hz), 7.31 (1H, d, J=2.7Hz), 7.49 (1H, s), 7.65 (1H, d, J=9.1Hz), 9.75 (1H, brd s) 10.99 (1H, s), 11.37 (1H, brd s); $^{13}$C NMR (75 MHz, DMSO-d$_6$) δ 10.07, 21.23, 21.61, 23.04, 34.69, 46.30, 50.87, 54.57, 59.86, 65.82, 107.52, 109.56, 118.02, 125.19, 126.45, 128.11, 138.07, 145.48, 154.44, 155.41; MS m/e 475 (MH ).

Anal. calcd. for C$_{24}$H$_{34}$N$_4$O$_4$S.2HCl.1.0H$_2$O:
C, 50.87; H, 6.78; N, 9.89.
Found: C, 50.86; H, 6.69; N, 9.91.

EXAMPLE 13

4[[3-8 2,3-Dihydro-2-oxo
-1H-imidazo[4,5-b]quinolin-7
yloxy]propyl]sulfonyl]-1-(2-methylpropyl)piperidine
dihydrochloride 17f.

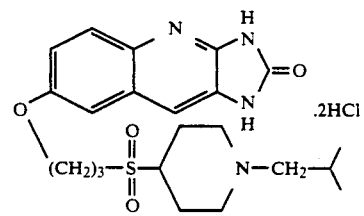

mp 323°-325° C.; IR (KBr, cm$^{-1}$) 3600-2400, 1738, 1368, 1308, 1230, 1134, 818; $^1$H NMR (300 MHz, DMSO-d$_6$) δ 0.93 (6H, d, J=6.2Hz), 2.05 (1H, m), 2.17 (6H, m), 2.83 (2H, m), 2.91 (2H, m), 3.31 (2H, m), 3.54 (3H, 4.15 (2H, m), 6.25 (2H, brd s), 7.17 (1H, d, J=8.4Hz), 7.36 (1H, s), 7.59 (1H, s), 7.72 (1H, d, J=8.4Hz), 10.18 (1H, brd s), 11.22 (1H, s); $^{13}$C NMR (75 MHz, DMSO-d$_6$) δ 20.82, 21.29, 21.62, 23.29, 46.30, 50.80, 54.72, 63.39, 65.92, 107.76, 110.54, 118.46, 125.55, 126.34, 127.03, 136.46, 145.05, 154.71, 155.23; MS m/e 447.

Anal. calcd. for C$_{22}$H$_{30}$N$_4$O$_4$S.2HCl.1.5H$_2$O:
C, 50.10; H, 6.28; N, 10.62.
Found: C, 50.09; H, 6.10; N, 10.39.

EXAMPLE 14

4-[[3-[2,3-Dihydro-2-oxo-
1H-imidazo[4,5-b]quinolin-7
-yl-oxy]propyl]sulfonyl]-1-(2-phenylethyl)piperidine
dihydrochloride 17h

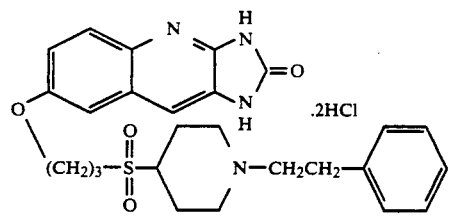

mp 305°-308° C.; IR (KBr, cm$^{-1}$) 3600-2300, 1762, 1300, 1234, 1132, 818, 756, 698; $^1$H NMR (300 MHz, DMSO-d$_6$) δ 2.18 (6H, m), 3.06 (4H, m), 3.24 (2H,,m), m), 3.55 (1H, m), 3.69 (2H, m), 4.19 (2H, t, J=6.0Hz), 7.27 (6H, m), 7.41 (1H, d, J=2.7 Hz), 7.65 s), 7.78 (1H, d, J=9.1 Hz), 8.9 (2H, brd, s) 11.3 (2H, brd s); $^{13}$C NMR (75 MHz, DMSO-d$_6$) δ 21.27, 21.85, 29.31, 46.40, 50.04, 54.61, 56.55, 65.93, 107.79, 110.90, 118.60, 125.65, 126.25, 126.54, 126.83, 128.70, 128.73, 135.75, 137.20, 144.82, 154.79, 155.11; MS m/e 495.

Anal. calcd. for C$_{26}$H$_{30}$N$_4$O$_4$S.2HCl.0.6 H$_2$O:
C, 54.00; H, 5.79; N, 9.69.

Found: C, 53.99; H, 5.64; N, 9.54.

EXAMPLE 15

1-(2-Cyclohexylethyl)-4-[[(3-[(2,3-dihydro-2-oxo-1H-imidazo[4,5-b]quinolin-7-yloxy]propyl]sulfonyl]piperidine dihydrochloride 17g

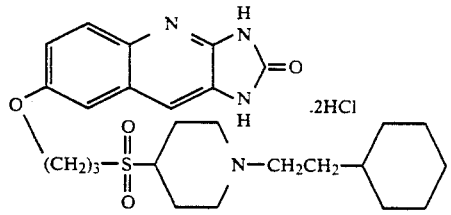

mp 314°-317° C.; IR (KBr, cm⁻¹) 3600-2400, 1728, 1296, 1240, 1128, 824; ¹H NHR (300 MHz, DMSO-d₆) δ 0.89 (2H, m), 1.16 (4H, m), 1.61 (7H, m), 2.07 m), 2.19 (4H, m), 2.92 (3H, m), 3.33 (3H, m), 3.52 m), 4.17 (2H, t, J=6.0Hz), 5.46 (2H, brd s), 7.1B (1H, dd, J=9.1 and 2.7Hz), 7.35 (1H, d, J=2.7Hz), 7.56 (1H, s), 7.71 (1H, d, J=9.1 Hz), 10.79 (1H, brd s), 11.13 (1H, s); ¹³C NMR (75 MHz, DMSO-d₆ δ 21.25, 21.79, 25.52, 25.92, 30.15, 32.39, 35.00, 46.33, 49.92, 54.18, 54.60, 65.83, 107.61, 110.11, 118.25, 125.35, 126.34, 127.41, 137.05, 145.17, 154.55, 155.25; MS m/e 501 (MH+).

Anal. caldc. for C₂₆H₃₆N₄O₄S.2HCL .0.68H₂O: C, 53.31; H, 6.77; N, 9.56. Found: C, 53.29; H, 6.48; N, 9.56.

EXAMPLE 16

4-[3-[2,3-Dihydro-2-oxo 1H-imidazo[4,5-b]quinolin-7-yl-oxy]propyl]sulfonyl]-1-[(3-trifluoromethylhenvlmethy phenylmethyl]piperidine dihydrochloride 17i

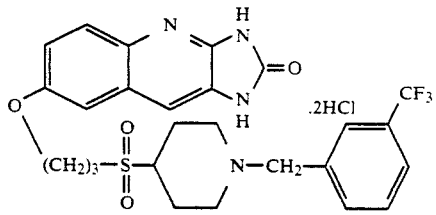

mp 283°-285° C.; IR (KHr, cm⁻¹) 3600-2300, 1726, 1330, 1296, 1242, 1128; ¹H NMR (300 MHz, DMSO-d₆) δ 2.11 (6H, m), 2.95 (2H, m), 3.31 (2H, t, J=7.2Hz), 3.47 (3H, m), 4.16 (2H, t, J=5.9Hz), 4.43 (2H, m), 4.77 (2H, m), 7.16 (1H, dd, J=9.1 and 2.7 Hz), 7.34 d, J=2.0Hz), 7.55 (1H, s), 7.68 (2H, m), 7.81 (1H, d, J=7.8Hz), 7.94 (1H, d, J=7.6Hz), 8.05 (!H, s), 11.11 (1H, s), 11.40 (1H, brd s); ¹³C NMR (75 MHz, DMSO-d₆) δ 21.23, 21.65, 4634. 49.70, 54.44, 57.87, 65.83, 107.58, 110.05, 118.21, 122.20, 125.33, 126.34, 127.47, 128.39, 129.17, 129.60, 129.85, 180.83, 135.84, 137.14, 145.20, 154.54, 155.27; MS m/e 549.

Anal. calcd. for C₂₆H₂₇F₃N₄O₄S.2HCl.0.98H₂O: C, 48.86; H, 4.88; N, 8.77. Found: C, 48.87; H, 4.77; N, 8.71.

EXAMPLE 17

4[[2,3-Dihydro-2-oxo-1H-imidazo[4,5-b]quinolin-7-yl-pxy]propyl]sulfonyl]-1-[(tetrahydro-2H-pyran-2-yl) piperidine dihydrochloride 17k

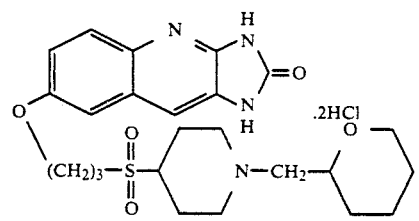

mp 221°-224° C.; IR (KBr, cm³¹ ¹) 3600-2400, 1730, 1294, 1264, 1240, 1130, 826; ¹NMR (300 MHz, DMSO-d₆) δ 1.15 (1 H, m), 1.46 (4 H, m), 1.75 (1 H, m), 2.06 (2 H, m), 2.19 (4 H, m), 3.03 (4 H, m), 3.36 (3 H, m), 3.53 (2 H, m), 3.65 (1 H, m), 3.84 (2 H, m), 4.17 (2 H, t, J = 6 Hz), 6.14 (2 H, brd s), 7.18 (1 H, dd, J =and 2.7 Hz), 7.36 (1 H, d, J =2.7 Hz), 7.57 (1 H, s), 7.72 (1 H, d, J =9.1 Hz), 10.55 (1 H, brd s), 11.16 (1 H, s); ¹³C NMR (75 MHz, DMSO-d₆) δ 15.19, 25.06, 28.78, 46.28, 50.54, 51.20, 54.41, 60.04, 64.93, 65.84, 67.18, 71.53, 107.62, 110.21, 118.28, 125.40, 126.32, 127.29, 136.87, 145.12, 154.57, 155.23; MS m/e 489 (MH+).

Anal. calcd. for C₂₄H₃₂N₄O₅S.2HCl .1.5H₂O: C, 49.04; H, 6.13; N, 9.53. Found: C, 49.03; H, 5.80; N, 9.72.

EXAMPLE 18

Ethyl 4[[3-[2,3-Dihydro-2-oxo-1H-imidazo[4,5-b]quinolin-7-yloxy]butyl]sulfonyl]-1-piperidine-carboxylate 13b

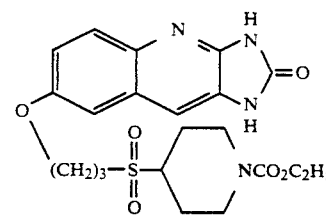

mp 289°-292° C.; IR (KBr, cm⁻¹) 3600-2400, 1726, 1692, 1364, 1248, 1222, 1124, 826; ¹NMR (300 MHZ, CF₃CO₂D) δ 0.92 (3H, t, J=7.1Hz), 1.46 (2H, m), 1.79 (6H, m), 2.60 (2H, t, J=12.3Hz), 2.90 (2H, m), 2.98 m), 3.84 (4H, m), 4.02 (2H, m), 7.07 (1H, d, J=2.4Hz), 7.20 (1H, dd, J=9.3 and 2.4Hz), 7.58 (1H, d, J=9.4Hz), 7.89 (1H, s); ¹³C NMR (CF₃CO₂D)δ 13.72, 18.61, 24.58, 28.01, 43.07, 49.82, 59.33, 63.98, 68.39, 109.06, 121.05, 121.79, 124.82, 125.99, 126.89, 128.02, 141.12, 155.41, 157.98, 158.97; MS m/e 477 (MH+).

Anal. calcd. for C₂₂H₂₈N₄O₆S. 0.47H₂O: C, 54.48; H, 6.01; N, 11.55. Found: C, 54.48; H, 5.93; N, 1.57.

EXAMPLE 19

4-[[2,3-Dihydro-2-oxo-1H-imidazo[4,5-b]quinolin-7-yloxy]butyl]sulfontl]piperidine dihydrochloride 18a

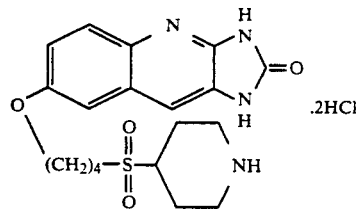

mp 235°–237° C.; IR (KBr, cm$^{-1}$) 3600–2300, 1736, 34, 826: $^1$H NMR (300 MHz, DMSO-d$_6$) δ 1.86 (6H, m),2.17 (2H, m), 2.92 (2H, m), 3.24 (2H, t, J=7.1 Hz), m), 3.47 (1H, m), 4.11 (2H, t, J=5.9Hz) 6.8-7.2 (1H, brd s), 7.21 (1H, dd, J=9.1 and 2.7Hz), H, d, J=2.7Hz), 7.62 (lH. s), 7.77 (1H, d, Hz), 9.10 (1H, brd s), 9.53 (1H, brd s), 11.26 1H, s); $^{13}$C NMR (75 MHz, DMSO-d$_6$) δ 19.74, 22.84, 29.06, 43.32, 50.40, 55.98, 68.80, 109.34, 112.42, 120.23, 127.24, 127.98, 128.30, 137.54, 146.48, 156.72, 156.82; MS m/e 405 (MH+).

Anal. calcd. for C$_{19}$H$_{24}$N$_4$O$_4$S.2HCl.1.3H$_2$O:
C, 45.56; H, 5.75; N, 11.19.
Found: C, 45.56; H, 5.28; N, 10.98.

EXAMPLE 20

4[[3-[2,3-Dihydro-2-oxo-1H-imidazo[4,5-b]quinolin-7-yloxyl]butylsulfonyl]-1-(phenylmethyl)piperidine dihydrochloride 18b

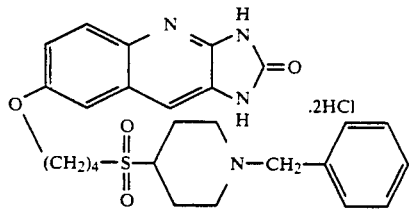

mp 228°–231° C.; IR (KBr, cm$^{-1}$) 3600–2300, 1726, 1294, 1240, 1130, 824, 746, 702: $^1$H NMR (300 MHz, DMSO-d$_6$) δ 1.88 (4H, m), 2.07 (2H, m), 2.15 (2H, m), m), 3.21 (2H, m], 3.41 (3H, m], 4.08 (2H, 4.26 (2H, m), 4.81 (2H, brd s), 7.17 (1H, dd, J=9.1 and 2.7Hz), 7.36 (lH, d, J=2.7Hz), 7.43 (3H, m), 7.57 (lH, s), 7.61 (2H, m), 7.71 (lH, d, J=9.1 Hz), 11.11 (1H, s), 11.22 (1H, brd s); $^{13}$C NMR (75 MHz, DMSO-d$_6$) δ 18.05, 21.69, 27.43, 48.87, 49.61, 54.51, 58.82, 67.10, 107.60, 110.26, 118.37, 125.43, 126.42, 127.27, 128.82, 129.52, 129.56, 131.66, 136.82, 54.94, 155.29; MS m/e 495 (MH+).

Anal. calcd. for C$_{26}$H$_{30}$N$_4$O$_4$S.2HCl:
C, 55.02; H, 5.68; N, 9.87.
Found: C, 54.86; H, 5.69; N, 9.60.

EXAMPLE 21

4-[[3-[2,3-Dihydro-2-oxo-1H-imidazo[4,5-b]qouinolin-7-yloxy]butylsulfonyl]1-[(4-fluorophenyl)methyl]piperidine dihydrochloride 18c

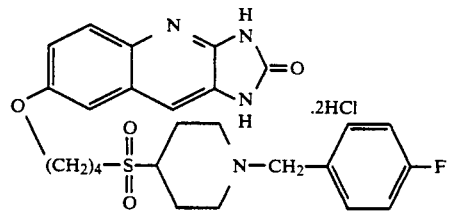

mp 207°–210° C.; IR (KBr, cm$^{-1}$) 3600–2300, 1736, 1296, 1228, 1130, 826: $^1$H NMR (300 MHz, DMSO-d$_6$) δ 1.82 (4H, m), 2.07 (2H, m), 2.17 (2H, m), 2.92 (2H, m), 3.22 (2H, m), 3.43 (3H, m), 4.08 (2H, m), 4.27 (2H, 5.67 (2H, brd S), 7.18 (lH, dd, J=9.1 and 2.7Hz), 7.28 (2H, t, J=8.7Hz), 7.37 (1H, d, J=2.7Hz), 7.58 (lH, s), 7.68 (2H, dd, J=8.6 and 5.5Hz), 7.72 (1H, d, Hz), 11.19 (1H, s), 11.33 (lH, brd s); $^{13}$C NMR (75 MHz, OMSO-d$_6$) δ 18.04, 21.67, 27.41, 48.85, 49.46, 54.47, 57.81, 67.10, 107.62, 110.42, 115.56, 115.84, 118.43, 125.47, 125.85, 126.37, 127.04, 133.99, 134.10, 144.99, 154.97, 155.24; MS m/e 513 (MH+).

Anal. calcd. for C$_{26}$H$_{29}$FN$_4$O$_4$S.2HCl. 0.5H$_2$O:
C, 52.52; H, 5.42; N, 9.42.
Found: C, 52.53; H, 5.25; N, 9.17.

EXAMPLE 22

1-(Cyclohexylmethyl)-4-[[3-[2,3-Dihydro-2-oxo-1H-imidaxo[4,5-b]quinolin-7-yloxy]butylsulfonyl piperidine dihydrochloride 18d

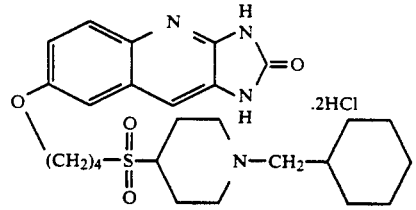

mp 311°–314° C.; IR (KBr, cm$^{-1}$) 3600–2300, 1742, 1294, 1238, 1130, 822: $^1$H NMR (300 MHz, DMSO-d$_6$) δ 0.93 (2H, m), 1.18 (3H, m), 1.63 (3H, m), 1.81 (3(4H, m), 2.19 (4H, m), 2.85 (2H, t, J=5.5Hz), 2.95 (2H, m), 3.25 (2H, m), 3.43 (1H, m), 3.58 (2H, m), 4.11 (2H, m), 6.12 (1H, brd s), 7.20 (lH, dd, J=9.1 and 2.7Hz), 7.40 (lH, d, J=2.7Hz), 7.61 (lH, s), 7.75 (lH, d, J=9.1Hz), 10.31 (lH, brd s), 11.23 (lH, s), 11.3–11.9 (lH, brd s); $^{13}$C NMR (75 MHz, DMSO-d$_6$) δ 18.00, 21.60, 25.03, 25.49, 27.39, 30.75, 32.09, 48.76, 50.76, 54.58, 62.19, 67.08, 107.62, 110.51 118.45, 125.49, 126.33, 126.87, 136.24, 144.90, 155.17; MS m/e 501 (MH+).

Anal. calcd. for C$_{26}$H$_{36}$N$_4$O$_4$S.2HCl. 1.5H$_2$O:
C, 52.06; H, 6.87; N, 9.34.
Found: C, 52.07; H, 6.29; N, 9.22.

EXAMPLE 23

4[[3-[2,3-Dihydro-2-oxo-1H-imidazo[4.5-b]qouinolin-7-yloxy]butylsulfonyl]-1-(2-ethylbut-1-yl)piperidine dihydrochloride 18e

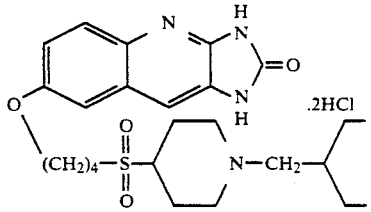

mp 241°–245° C.; IR (KBr, cm$^{-1}$) 3600–2300, 1742, 1296, 1238, 1130, 822; $^1$H NMR (300 MHz, DMSO-d$_6$) δ 0.84 (6H, t, J=7.3HZ), 1.35 (4H, m), 1.72 (1H, m), 1.91 (4H, m), 2.19 (4H, m), 2.91 (2H, t, J=5.7Hz), 2.97 (2H, m), 3.26 (2H, m), 3.41 (1H, m), 3.62 (2H, m), 4.11 (2H, m), 5.8 (1H, brd s), 7.20 (1,H, dd, J=9.1 and 2.7Hz), 7.40 (1H, d, J=2.7Hz), 7.60 (lH, s), 7.74 (1H, d, J=9.1Hz), 9.94 (1H, brd s), 11.19 (1H, s), 11.2–11.8 (1H, brd s); $^{13}$C NMR (75 MHz, DMSO-d$_6$) δ 10.10, 18.01, 21.60, 23.11, 27.41, 34.70, 48.80, 50.83, 54.51, 59.87, 67.10, 107.63, 110.43, 118.43, 125.46, 126.36, 127.01, 136.44, 144.97, 154.97, 155.22; MS m/Ⓡ489 (MH+).

Anal. ca)cd. for C$_{25}$H$_{36}$N$_4$O$_4$S.2HCl. 2.OH$_2$O:
C, 50.34; H, 7.08; N, 9.39.
Found: C, 50.32; H, 6.58; N, 9.46.

What is claimed is:

1. A compound of the formula

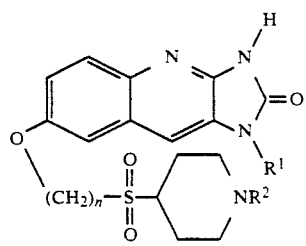

wherein
e$^1$ is H, or C$_1$-C$_4$ lower alkyl;
R$^2$ is H, or (CH$_2$)$_m$R$^3$;
R$^3$ is tetrahydro-2H-pyranyl, C$_1$-C$_8$ alkyl, C$_4$-C$_8$ cycloalkyl, or substituted or unsubstituted phenyl in which the substituents are halogen, alkoxy, or trifluoromethyl;
m is an integer of 1-3; and
n is an integer of 1-5; or pharmaceutically acceptable salt thereof.

2. The intermediate compound which is ethyl 4-[[3-[(2-,3- dihydro-2-oxo-1H-imidazo[4,5-b]quinolin-7-yl)oxy]propylsulfonyl]-1-piperidinecarboxylate.

3. The compound of claim 1 which is 4-[[3-dihydro-2-oxo-1H-imidazo[4,5-b]quinolin-7-yl)oxy]propylsulfonyl]piperidine or pharmaceutically acceptable salt thereof.

4. The compound of claim 1 which is 4-[[3-[2,3-dihydro-2-oxo-1H-imidazo[4,5-b]quinolin-7-yloxy]propyl]-sulfonyl]-1-(phenylmethyl)piperidine or pharmaceutically acceptable salt thereof.

5. The compound of claim ! which is 4-[[3-[2,3-dihydro-2-oxo-1H-imidazo[4,5-b]quinolin-7-yloxy]propyl]-sulfonyl]-1-(4-fluorophenylmethyl)piperidine or pharmaceutically acceptable salt thereof.

6. The compound of claim 1 which is 4-[[3-[2,3-dihydro-2-oxo-1H-imidazo[4,5-b]quinolin-7-yl-oxy]propyl]-sulfonyl]-1-(cyclohexylmethyl)piperidine or pharmaceutically acceptable salt thereof.

7. The compound of claim 1 which is 4-[[3-[2,3-dihydro-2-oxo-1H-imidazo[4,5-b]quinolin-7-yl-oxy]propyl]-sulfonyl]-1-(2-ethylbut-1-yl)piperidine or pharmaceutically acceptable salt thereof.

8. The compound of claim 1 which is 4-[[3-[2,3-dihydro-2-oxo-1H-imidazo[4,5-b]quinolin-7-yloxy]propyl]-sulfonyl]-1-(2-methylpropyl)piperidine or pharmaceutically acceptable salt thereof.

9. The compound of claim 1 which is 4-[[3-[2,3-dihydro-2-oxo-1H-imidazo[4,5-b]quinolin-7-yl-oxy]propyl]-sulfonyl]-1-(2-phenylethyl)piperidine or pharmaceutically acceptable salt thereof.

10. The compound of claim 1 which is 1-(2-cyclohexyethyl)-4-[[(3-[(2,3-dihydro-2-oxo-1H-imidazo [4,5-b]quinolin-7-yloxy]propyl]sulfonyl]piperidine or pharmaceutically acceptable salt thereof.

11. The compound of claim 1 which is 4-[[3-[2,3-dihydro-2-oxo-12H-imidazo[4,5-b]quinolin-7-yl-oxy]-propyl]sulfonyl]-1-[(3-trifluoromethylphenylmethyl]-piperidine or pharmaceutically acceptable salt thereof.

12. The compound of claim 1 which is 4-[[3-[2,3-dihydro-2-oxo-1H-imidazo[4,5-b]quinolin-7-yl-oxy]-propyl]sulfonyl]-1-[(tetrahydro-2H-pyran-2-yl) piperidine or pharmaceutically acceptable salt thereof.

13. The intermediate compound which is ethyl 4-[[3-[2,3-dihydro-2-oxo-1H-imidazo [4,5-b]quinolin-7-yloxy]butyl]sulfonyl]-1-piperidine-carboxylate.

14. The compound of claim 1 which is 4-[[3-[2,3-dihydro-2-oxo-1H-imidazo[4,5-b]quinolin-7-yloxy]butyl]sulfonyl]piperidine or pharmaceutically acceptable salt thereof.

15. The compound of claim 1 which is 4-[[3-[2,3-dihydro-2-oxo-1H-imidazo[4,5-b]quinolin-7-yloxy]butylsulfonyl]-1-(phenylmethyl)piperidine or pharmaceutically acceptable salt thereof.

16. The compound of claim 1 which is 4-[[3-[2,3-dihydro-2-oxo-1H-imidazo[4,5-b]quinolin-7-yloxy]butylsulfonyl]-1-[(4-fluorophenyl)methyl]piperidine or pharmaoeutioally acceptable salt thereof.

17. The compound of claim 1 which is 1-(cyclohexylmethyl)-4-[[3-[2,3-dihydro -2-oxo-1H-imidazo[4,5-b]quinolin-7-yloxy]butylsulfonyl]piperidine or pharmaceutically acceptable salt thereof.

18. The compound of claim 1 which is 4-[[3-[2,3-dihydro-2-oxo-1H-imidazo[4,5-b]quinolin-7 yloxy]-butylsulfonyl]-1-(2-ethylbut-1-yl)piperidine or pharmaceutically acceptable salt thereof.

19. A method for inhibiting blood platelet aggregation in a mammal which comprises administering a therapeutically effective amount of a compound of claim 1 or a pharmaceutically acceptable salt thereof.

20. The pharmaceutical composition for inhibiting blood platelet aggregation comprising a therapeutically effective amount of a compound of claim 1 of a pharmaceutically acceptable acid addition salt thereof and a pharmaceutical carrier.

* * * * *

UNITED STATES PATENT AND TRADEMARK OFFICE
CERTIFICATE OF CORRECTION

PATENT NO. : 5,158,958
DATED : October 27, 1992
INVENTOR(S) : Hewawasam, et al

It is certified that error appears in the above-indentified patent and that said Letters Patent is hereby corrected as shown below:

Column 25, Claim 1, line 49 after "wherein" delete "$e^1$" and insert --$R^1$--.

Column 25, Claim 3, line 62 after "4-[[3-" insert --[(2-,3---.

Column 26, Claim 5, line 3 after "claim" delete "!" and insert --1--.
Column 26, Claim 16, line 48 after "or" delete "pharmaoeutioally" and insert --pharmaceutically--.

Signed and Sealed this

Twelfth Day of October, 1993

Attest:

BRUCE LEHMAN

Attesting Officer

Commissioner of Patents and Trademarks